United States Patent [19]

Rigby

[11] 4,065,386

[45] Dec. 27, 1977

[54] ALGAE GROWTH CONTROL

[75] Inventor: Robert Alexander Rigby, Canterbury, Australia

[73] Assignee: Algard Pty. Ltd., Balwyn, Australia

[21] Appl. No.: 696,502

[22] Filed: June 16, 1976

[30] Foreign Application Priority Data

Dec. 10, 1975  Australia ............................. 4244/75

[51] Int. Cl.² ............................................. C02B 3/02
[52] U.S. Cl. ........................................ 210/60; 210/64
[58] Field of Search ...................... 210/42 S, 222, 223,
210/60, 64; 71/67; 162/161; 21/54 R; 204/155, 156

[56] References Cited

U.S. PATENT DOCUMENTS

| 3,594,115 | 7/1971 | Wesley et al. | 210/64 |
| 3,714,037 | 1/1973 | Almasi et al. | 210/42 S |

Primary Examiner—Thomas G. Wyse
Attorney, Agent, or Firm—Jack M. Wiseman

[57] ABSTRACT

A method of treating water to control or eliminate algae and bacterial growth wherein the water is passed through a magnetic field. The magnetic field is generally normal to the direction of flow of the water.

6 Claims, 4 Drawing Figures

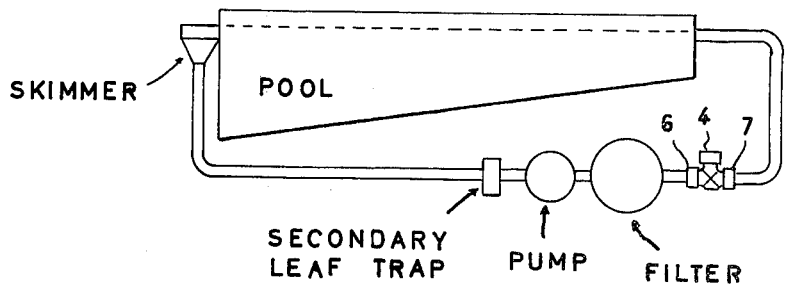
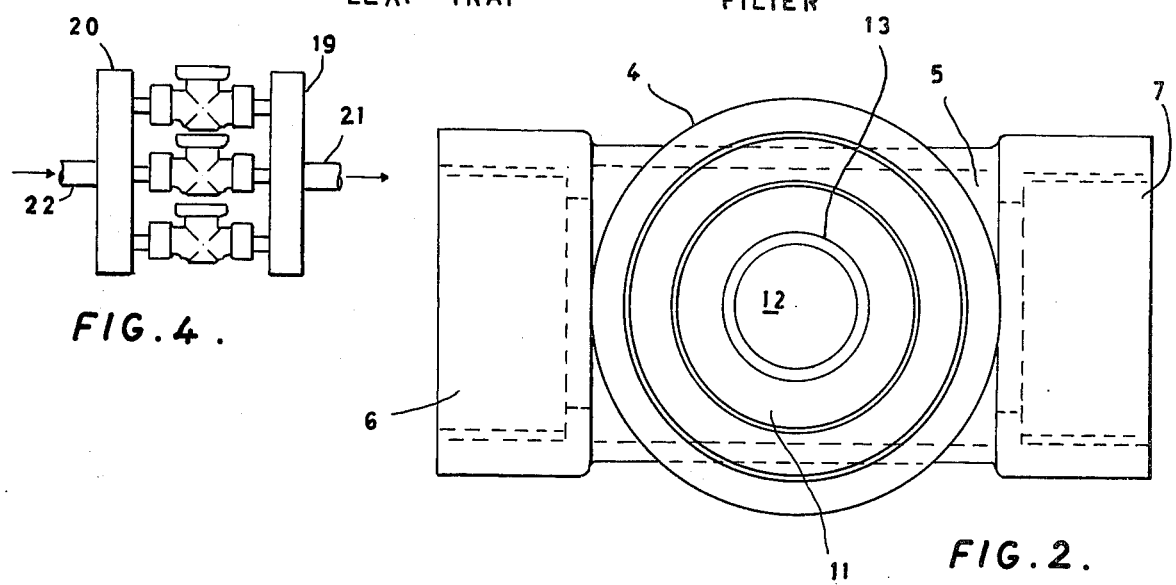
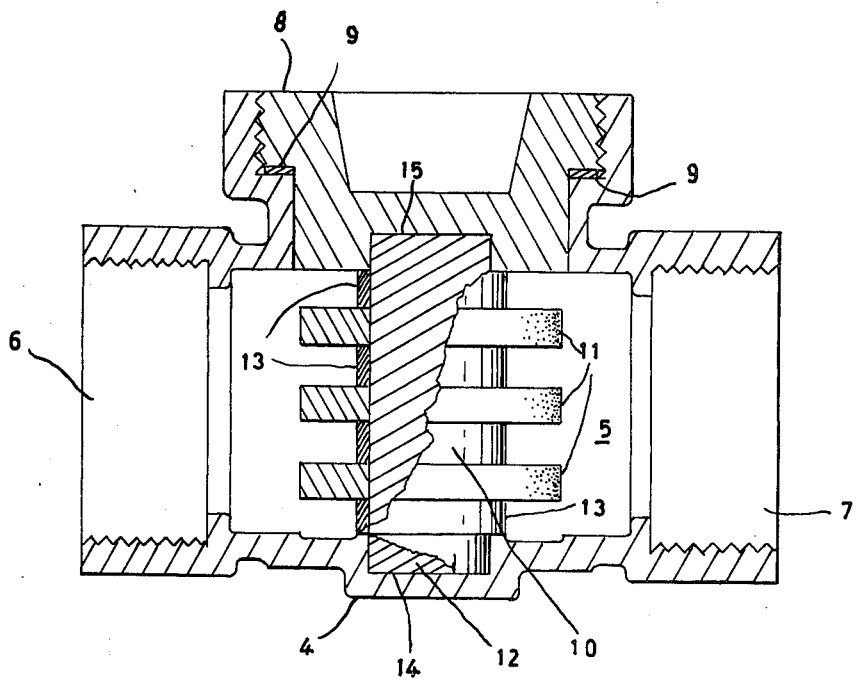

ALGAE GROWTH CONTROL

This invention relates to the control of algae growth in water systems such as cooling towers, swimming pools and the like.

The presence and rapid multiplication of algae organisms in water systems, particularly where water recirculation is involved constitutes a serious economic problem requiring constant attention in industrial systems, and a substantial nuisance in public and private swimming pools.

Whilst the use of chemical additives is effective in this application continuous surveillance is necessary as the chemicals are only effective for a limited time in any given situation.

It is accordingly the principal objective of this invention to provide a simple and effective means for controlling algae growth requiring minimum attention to maintain its effectiveness.

With the above stated principal objective in view there is provided according to the invention a method of controlling the propagation and growth of algae in water systems comprising the steps of passing the water through a strong magnetic field.

The use of magnetic fields in water treatment has been previously proposed in relation to descaling of pipes and water boilers and in removing ferrous crystals from aqueous liquids. However, there has been no suggestion previously to treat water which is used for sanitary or domestic use in order to reduce the amount of chemical additives required to control bacteriological growth and in particular algae growth.

The applicant has found that the effect of the magnetic field on the water is such as to almost completely render the water unsuitable for the propagation and growth of algae, and certainly to a degree in marked contrast with prior methods.

There is further provided according to the invention apparatus for use in the control of the propagation and growth of algae in water systems comprising a duct member for insertion in the system, including means for establishing a strong magnetic field within the duct such that water passing through the duct traverses said magnetic field.

More particularly the device comprises a duct member incorporated in a water supply duct. Magnetic means disposed within said duct member which creates a magnetic field transverse to the lengthwise direction of the duct. It is equally possible to incorporate permanent or electrogmagnets about the periphery of the duct and this is particularly desirable where separation of the magnetic material from the aqueous liquid is required.

In one practical arrangement of the apparatus of the invention a brass or plastic tube is provided having its bore threaded at each extremity for connection with conventional water recirculation pipes. Located within the tube in spaced disposition across its diameter is an array of toroidal permanent magnets to establish the desired magnetic field within the tube whilst permitting the ready passage of water therethrough.

Alternatively the arrangement may comprise a length of tubing of any suitable known plastics material and the magnetic field may be generated by permanent magnets mounted on the exterior of the tube, or by an electromagnet device surrounding the tube or duct.

Generally a small permanent magnet fitted transversely within a 1½ inch duct member is sufficient to treat water passing through at normal flow rates such as those encountered in domestic swimming pool filter circuits. Where larger ducting is employed then the magnets can be increased in capacity. Alternatively a manifold can be inserted incorporating several of the smaller units. For example a 3 inch duct can be fitted with a manifold incorporating four magnetic units designed for a 1½ inch duct.

Conveniently the magnetic unit is inserted in the inlet to the water storage. In swimming pools the unit can be installed in the filter circuit between the filters and the return inlet to the pool.

The method of this invention may not rid the water supply of bacteria and thus chemical treatment, e.g. with chlorine, may still be required although in smaller quantities. In summer or in warm weather the chlorine addition is necessary but in cold weather the device of this invention may be sufficiently effective on its own so that no chlorine is required.

There will now be described a preferred embodiment of this invention.

FIG. 1 illustrates a cross sectional view of a treatment unit according to this invention.

FIG. 2 is a plan view of the device shown in FIG. 1.

FIG. 3 illustrates a typical filter circuit for a swimming pool, and

FIG. 4 illustrates a manifold arrangement.

The unit 4 includes a central chamber 5 and an inlet 6 and outlet 7 each of which is screw threaded and adapted for connection to water ducts. The body is composed of brass although plastic is equally suitable.

A plug 8 enables access to be made to chamber 5 and washer 9 provides a seal for this opening. Within chamber 5 is disposed the magnetic unit 10. This unit 10 is composed of 3 annular ceramic ferrite permanent magnets 11 mounted on a plastic shaft 12 and are spaced apart by annular spacers 13. The plastic spacers 13 are slidable onto the shaft 12 as are the magnets so that the magnetic unit is easily assemblied.

Recesses 14 and 15 accommodate the ends of the shaft 12 and the height of chamber 5 is such as to ensure a secure fit of the magnetic unit 10 within the chamber 5. The magnetic unit 10 is aligned to produce a magnetic field which is at right angles to the axis through the inlet 6 and outlet 7.

FIG. 3 illustrates the positioning of the device 4 in the filter circuit of a pool. Similar positioning can be used when the device is used for water storage tanks or air conditioning plants.

In FIG. 4 there is illustrated a manifold construction whereby several devices 4 as shown in FIGS. 1 and 2 can be used where high flow rates or large diameter pipes are used. The manifolds 19 and 20 are designed to accomodate several devices 4 between them and are adapted for connection to water ducts via the outlets 21 and 22.

The present invention can be used where ever algae growth is likely to occur in water storages and although particularly useful in swimming pools can be used in air conditioning plants, fountains and garden rockpools and water supply reservoirs.

It has been found that where the water to be treated has a high nitrogen content the invention is not as effective in combatting algae growth. A secondary result of the use of this invention is sedimentation resulting from a precipitation of certain minerals present as impurities in the water. This in no way effects the performance of the method of this invention.

We claim:

1. A method for treating water disposable in an open, uncovered storage to inhibit the growth of algae and bacteria therein comprising the steps of:
   a. conducting the water along a predetermined path to open, uncovered storage; and
   b. producing a magnetic field in said predetermined path of sufficient strength to inhibit the growth of algae and bacteria in said water.

2. A method as claimed in claim 1 wherein said magnetic field is disposed across said predetermined path at right angles to the direction of flow of said water to said storage.

3. A method as claimed in claim 2 wherein said magnetic field is produced by a permanent magnet disposed in said predetermined path for the passage of said water thereover.

4. A method as claimed in claim 2 and comprising the step of circulating said water from said storage, through a filtration unit and said magnetic field, and back to said storage.

5. A method as claimed in claim 4 wherein said magnetic field is produced by a permanent magnet disposed in said predetermined path for the passage of said water thereover.

6. A method as claimed in claim 1 and comprising the step of circulating said water from said storage, through a filtration unit, and back to said storage.

REEXAMINATION CERTIFICATE (502nd)
United States Patent [19]
Rigby

[11] B1 4,065,386
[45] Certificate Issued May 13, 1986

[54] ALGAE GROWTH CONTROL

[75] Inventor: Robert A. Rigby, Canterbury, Australia

[73] Assignee: Algarid Pty. Ltd., Balwyn, Australia

Reexamination Request:
No. 90/000,723, Feb. 19, 1985

Reexamination Certificate for:
Patent No.: 4,065,386
Issued: Dec. 27, 1977
Appl. No.: 696,502
Filed: Jun. 16, 1976

[30] Foreign Application Priority Data
Dec. 10, 1975 [AU] Australia .............. 4244/75

[51] Int. Cl.⁴ ............................. C02F 1/48
[52] U.S. Cl. .................................. 210/695
[58] Field of Search ........... 210/695, 748, 764, 765

[56] References Cited
U.S. PATENT DOCUMENTS

| | | |
|---|---|---|
| 531,183 | 12/1894 | Harris . |
| 2,885,081 | 5/1959 | Stem ................................ 210/222 |
| 3,228,878 | 1/1966 | Moody ............................. 210/57 |
| 3,345,594 | 10/1967 | Vermeiren ........................ 335/306 |
| 3,347,211 | 10/1967 | Falkenberg et al. ............... 119/5 |
| 3,594,115 | 7/1971 | Wesley et al. ..................... 21/54 |
| 3,669,274 | 6/1972 | Happ et al. ....................... 210/222 |
| 3,680,705 | 8/1972 | Happ et al. ....................... 210/222 |
| 3,714,037 | 1/1973 | Almasi et al. .................... 210/42 |
| 3,923,660 | 12/1975 | Kottmeier ........................ 210/222 |

OTHER PUBLICATIONS

Corrosion Technology, Jul. 1958, Magnetic Treatment of Liquids for Scale and Corrosion Prevention by Theo Vermeiren.

*Primary Examiner*—Thomas G. Wyse

[57] ABSTRACT

A method of treating water to control or eliminate algae and bacterial growth wherein the water is passed through a magnetic field. The magnetic field is generally normal to the direction of flow of the water.

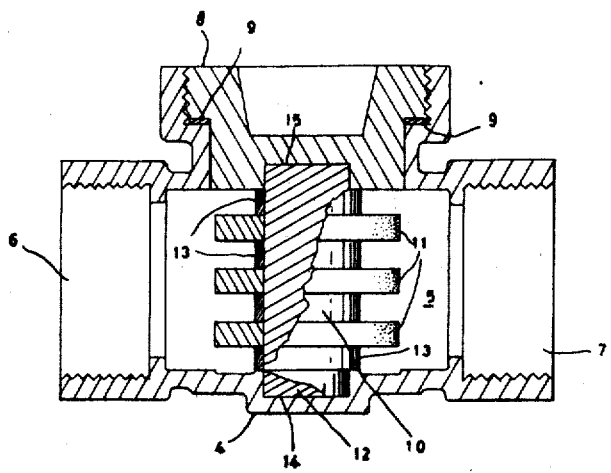

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in in italics indicates additions made to the patent.

AS A RESULT OF REEXAMINATION, IT HAS BEEN DETERMINED THAT:

The patentability of claims 4–6 is confirmed.

Claims 1–3 are cancelled.

New claims 7 and 8 are added and determined to be patentable.

7. *A method as claimed in claim 6 wherein said magnetic field is disposed across said predetermined path at right angles to the direction of flow of said water to said storage.*

8. *A method as claimed in claim 6 wherein said magnetic field is produced by a permanent magnet disposed in said predetermined path for the passage of said water thereover.*

* * * * *